(12) United States Patent
Lu et al.

(10) Patent No.: US 7,749,222 B2
(45) Date of Patent: Jul. 6, 2010

(54) BIPOLAR FORCEPS

(75) Inventors: Ifung Lu, Cincinnati, OH (US); Gary L. Long, Cincinnati, OH (US); Omar Vakharia, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1003 days.

(21) Appl. No.: 11/438,130

(22) Filed: May 19, 2006

(65) Prior Publication Data

US 2007/0270798 A1 Nov. 22, 2007

(51) Int. Cl.
*A61B 18/18* (2006.01)

(52) U.S. Cl. .............................. 606/51; 606/50; 606/52; 606/205; 606/206; 606/207

(58) Field of Classification Search ................... 604/22; 606/48–52, 205
See application file for complete search history.

(56) References Cited

U.S. PATENT DOCUMENTS

| | | | | |
|---|---|---|---|---|
| 3,964,477 A | * | 6/1976 | Ellis et al. ..................... | 604/20 |
| 4,269,174 A | | 5/1981 | Adair | |
| 4,576,161 A | | 3/1986 | Mikkelson | |
| 5,192,280 A | | 3/1993 | Parins | |
| 5,330,471 A | * | 7/1994 | Eggers ......................... | 606/48 |
| 5,403,311 A | | 4/1995 | Abele et al. | |
| 5,484,436 A | * | 1/1996 | Eggers et al. .................. | 606/48 |
| 5,674,220 A | * | 10/1997 | Fox et al. ...................... | 606/51 |
| 5,720,718 A | | 2/1998 | Rosen et al. | |
| 5,782,859 A | | 7/1998 | Nicholas et al. | |
| 5,849,022 A | * | 12/1998 | Sakashita et al. ............ | 606/174 |
| 6,022,334 A | | 2/2000 | Edwards et al. | |
| 6,071,281 A | * | 6/2000 | Burnside et al. .............. | 606/41 |
| 6,086,586 A | * | 7/2000 | Hooven ........................ | 606/50 |
| 6,273,887 B1 | * | 8/2001 | Yamauchi et al. ............. | 606/48 |
| 6,280,458 B1 | * | 8/2001 | Boche et al. ................ | 606/206 |
| 6,379,349 B1 | | 4/2002 | Mueller et al. | |
| 6,394,998 B1 | | 5/2002 | Wallace et al. | |
| 6,428,538 B1 | | 8/2002 | Blewett et al. | |
| 6,447,506 B1 | | 9/2002 | Swanson et al. | |
| 6,638,275 B1 | | 10/2003 | McGaffigan et al. | |
| 6,669,696 B2 | * | 12/2003 | Bacher et al. ................. | 606/51 |
| 6,767,349 B2 | * | 7/2004 | Ouchi ........................ | 606/51 |
| 6,770,072 B1 | * | 8/2004 | Truckai et al. ................ | 606/52 |
| 6,918,906 B2 | | 7/2005 | Long | |
| 6,969,389 B2 | | 11/2005 | Kidooka | |

(Continued)

FOREIGN PATENT DOCUMENTS

EP 0997108 5/2000

*Primary Examiner*—Linda C Dvorak
*Assistant Examiner*—Amanda Scott
(74) *Attorney, Agent, or Firm*—Victor C. Moreno (57) ABSTRACT

A surgical system including a source of electrical energy, the source including a first electrical connection and a second electrical connection, a first jaw member including a first electrode connected thereto and electrically isolated therefrom, the first electrode being electrically connected to the first electrical connection, a second jaw member pivotally connected to the first jaw member and including a second electrode connected thereto and electrically isolated therefrom, the second electrode being electrically connected to the second electrical connection and electrically isolated from the first electrode, and an elongated shaft having a distal end and a proximal end, wherein the first jaw member and the second jaw member are connected to the distal end of the shaft.

13 Claims, 9 Drawing Sheets

U.S. PATENT DOCUMENTS

| | | | |
|---|---|---|---|
| 6,980,854 B2 * | 12/2005 | Bernabei | 604/20 |
| 7,278,992 B2 | 10/2007 | Cropper et al. | |
| 2002/0002385 A1 * | 1/2002 | Boche et al. | 606/205 |
| 2003/0078577 A1 * | 4/2003 | Truckai et al. | 606/51 |
| 2003/0191465 A1 * | 10/2003 | Yahagi et al. | 606/48 |
| 2004/0030335 A1 | 2/2004 | Zenati et al. | |

* cited by examiner

BIPOLAR FORCEPS

FIELD OF THE INVENTION

The present application relates to medical devices and systems and, more particularly, to medical devices and systems for coagulating tissue with electrical energy.

BACKGROUND OF THE INVENTION

Bleeding in the gastrointestinal ("GI") tract may be associated with various ulcers, lesions, cancers and the like. For example, peptic ulcers in the upper GI tract have been identified as a common cause of GI bleeding. If left untreated, GI bleeding may lead to anemia-like symptoms (e.g., fatigue, dizziness and chest pain), hepatic encephalopathy, hepatorenal syndrome, shock and death.

Successful treatment of GI bleeding typically includes addressing the cause of the bleeding and/or haemostasis. For example, peptic ulcers may be associated with an infection of *Helicobacter pylori* and, therefore, may require treatment of the infection to reduce the risk of re-bleeding coupled with tissue coagulation to achieve haemostasis.

Haemostasis may be achieved by invasive surgery or by various less invasive endoscopic techniques, such as laser treatment, bipolar or monopolar electrocautery, heat probing, injections with sclerosing agents (e.g., epinephrine) or mechanical tamponade with mechanical clips, for example. While prior art haemostasis techniques have presented some success, physicians continue to seek improved techniques for achieving haemostasis using endoscopic procedures.

Accordingly, there is a need for an improved apparatus, system and method for providing mechanical tamponade and supplying electrical energy to target tissue during an endoscopic procedure.

SUMMARY OF THE INVENTION

One aspect of the disclosed surgical device may include an elongated shaft having a distal end and a proximal end, a first jaw member pivotally connected to the distal end of the shaft, the first jaw member including a first electrode connected thereto and electrically isolated therefrom, a second jaw member pivotally connected to the distal end of the shaft and moveable relative to the first jaw member between an open configuration and a closed configuration, the second jaw member including a second electrode connected thereto and electrically isolated therefrom, and a handle assembly connected to the proximal end of the shaft, the handle assembly including an actuator operatively connected to at least one of the first and second jaw members to facilitate movement of the first and second jaw members to the closed configuration.

One aspect of the disclosed surgical system may include a source of electrical energy, the source including a first electrical connection and a second electrical connection, a first jaw member including a first electrode connected thereto and electrically isolated therefrom, the first electrode being electrically connected to the first electrical connection, a second jaw member pivotally connected to the first jaw member and including a second electrode connected thereto and electrically isolated therefrom, the second electrode being electrically connected to the second electrical connection and electrically isolated from the first electrode, and an elongated shaft having a distal end and a proximal end, wherein the first jaw member and the second jaw member are connected to the distal end of the shaft.

In another aspect, the disclosed surgical system may include a source of electrical energy, the source including a first electrical connection and a second electrical connection, a first jaw member including a first electrode and a first portion of absorbent material positioned over at least a portion of the first electrode, the first electrode being electrically connected to the first electrical connection, a second jaw member pivotally connected to the first jaw member and including a second electrode and a second portion of absorbent material positioned over at least a portion of the second electrode, the second electrode being electrically connected to the second electrical connection and electrically isolated from the first electrode, and an elongated shaft having a distal end and a proximal end, wherein the first jaw member and the second jaw member are connected to the distal end of the shaft, wherein the first jaw member is adapted to pivot relative to the second jaw member to clamp tissue positioned therebetween and to approximate the first electrode toward the second electrode.

One aspect of the disclosed method for treating a target tissue in a gastrointestinal tract of a patient may include the steps of providing an endoscope having a working channel extending therethrough, providing a surgical device including a first jaw member and a second jaw member pivotally connected to the first jaw member, the first and second jaw members being disposed on a distal end of an elongated shaft, wherein the first jaw member includes a first electrode and the second jaw member includes a second electrode, positioning the endoscope in the gastrointestinal tract of the patient to provide endoscopic access to the target tissue, passing the surgical device through the working channel of the endoscope, pivoting the first jaw member relative to the second jaw member to grasp the target tissue therebetween, thereby positioning the target tissue between the first and second electrodes, and passing electrical energy between the first second electrodes when the target tissue is positioned therebetween.

Other aspects of the disclosed bipolar forceps and associated systems and methods will become apparent from the following description, the accompanying drawings and the appended claims.

DETAILED DESCRIPTION OF THE INVENTION

Figure 1:
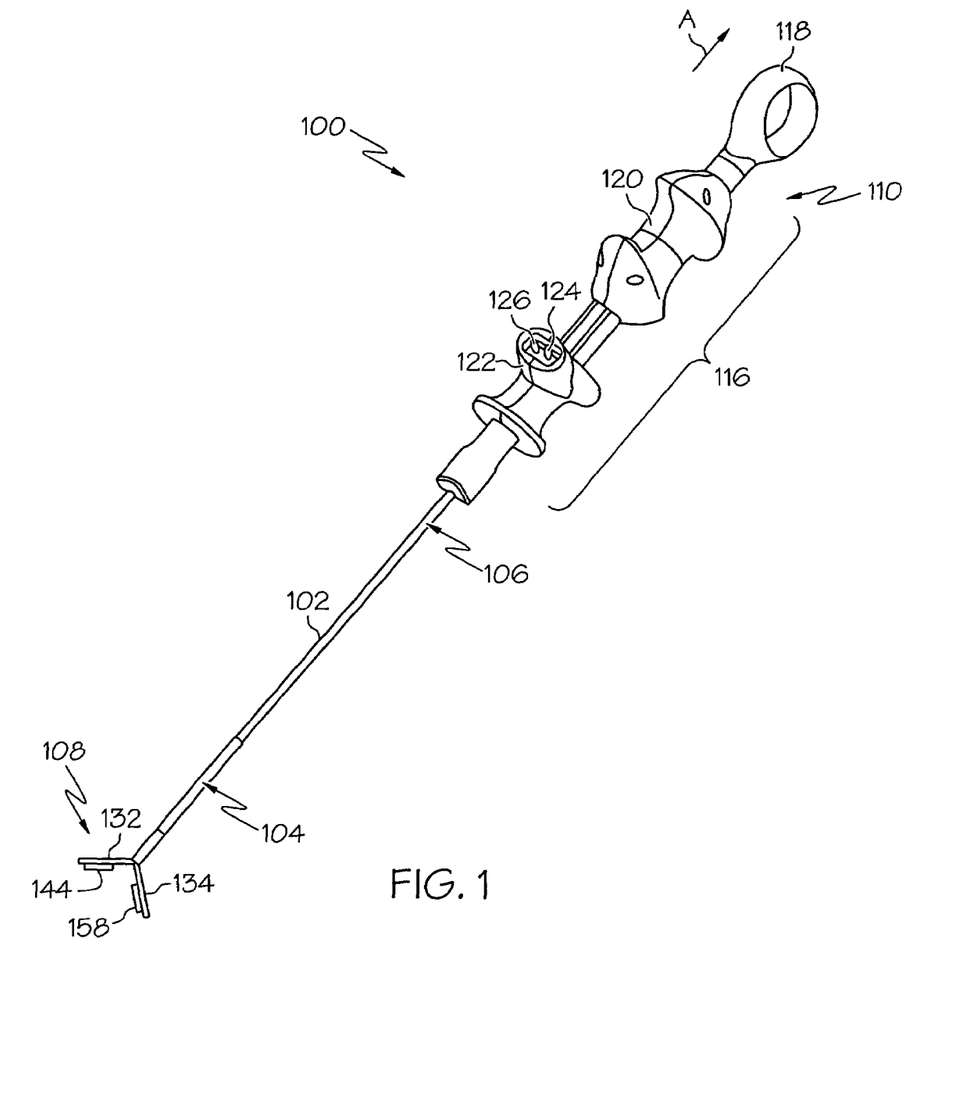
FIG. 1 is a perspective view of one aspect of the disclosed bipolar forceps.

Referring to FIG. 1, one aspect of the disclosed bipolar forceps, generally designated 100, may include an elongated shaft 102 having a distal end 104 and a proximal end 106, a grasping/coagulation assembly 108 disposed at the distal end 104 of the shaft 102 and a handle assembly 110 disposed at the proximal end 106 of the shaft 102. The shaft 102 may be flexible and may mechanically connect the grasping/coagulation assembly 108 to the handle assembly 110. The shaft 102 and the grasping/coagulation assembly 108 of the forceps 100 may be sized and shaped to pass through a working channel 112 of a flexible endoscope 114 (FIG. 8), thereby providing the device 100 with endoscopic access to target tissue 115 (e.g., peptic ulcers in the GI tract).

Figure 2:
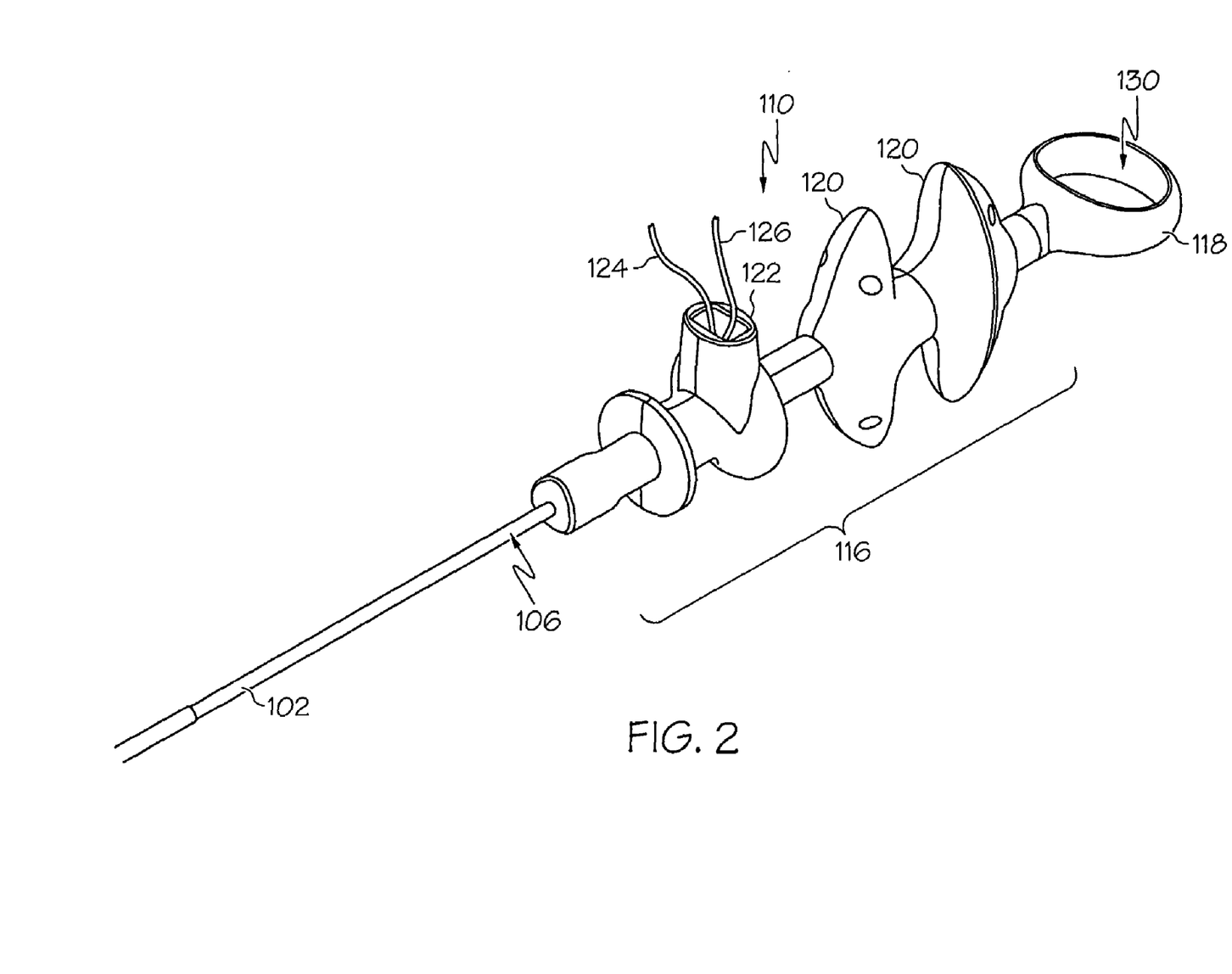
FIG. 2 is a perspective view of one aspect of the user end of the bipolar forceps of FIG. 1.
Figure 8:
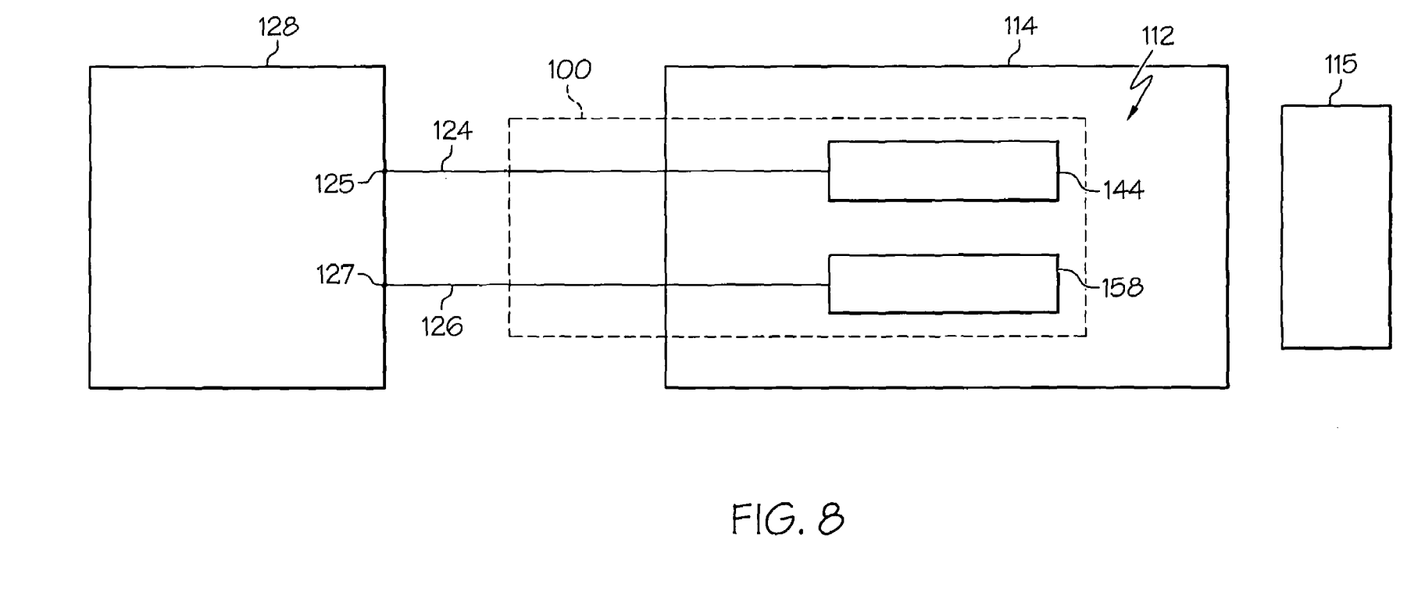
FIG. 8 is a block diagram of one aspect of a surgical system including the device of FIG. 1.

As shown in FIG. 2, one aspect of the handle assembly 110 may include a base portion 116 and an actuator 118. The actuator 118 may include an opening 130 sized to receive a finger (not shown), such as a thumb, of a user and may be connected (e.g., mechanically) to the grasping/coagulation assembly 108 to actuate the grasping/coagulation assembly 108 (e.g., facilitate grasping) in response to movement of the actuator 118. The base portion 116 may include a finger gripping portion 120 and an electrical connection portion 122 including a first electrode wire 124 and a second electrode wire 126. The electrode wires 124, 126 may extend through the shaft 102 and, as shown in FIG. 8, may connect the device 100 to a source of electrical energy (e.g., an Erbe ICC 200 electrosurgical generator) 128 at electrical connection points 125, 127. The finger gripping portion 120 may allow a user to securely grasp the base portion 116 of the device 100 with, for example, a middle finger and a forefinger, while the user manipulates the actuator 118 with a thumb.

Figure 3:
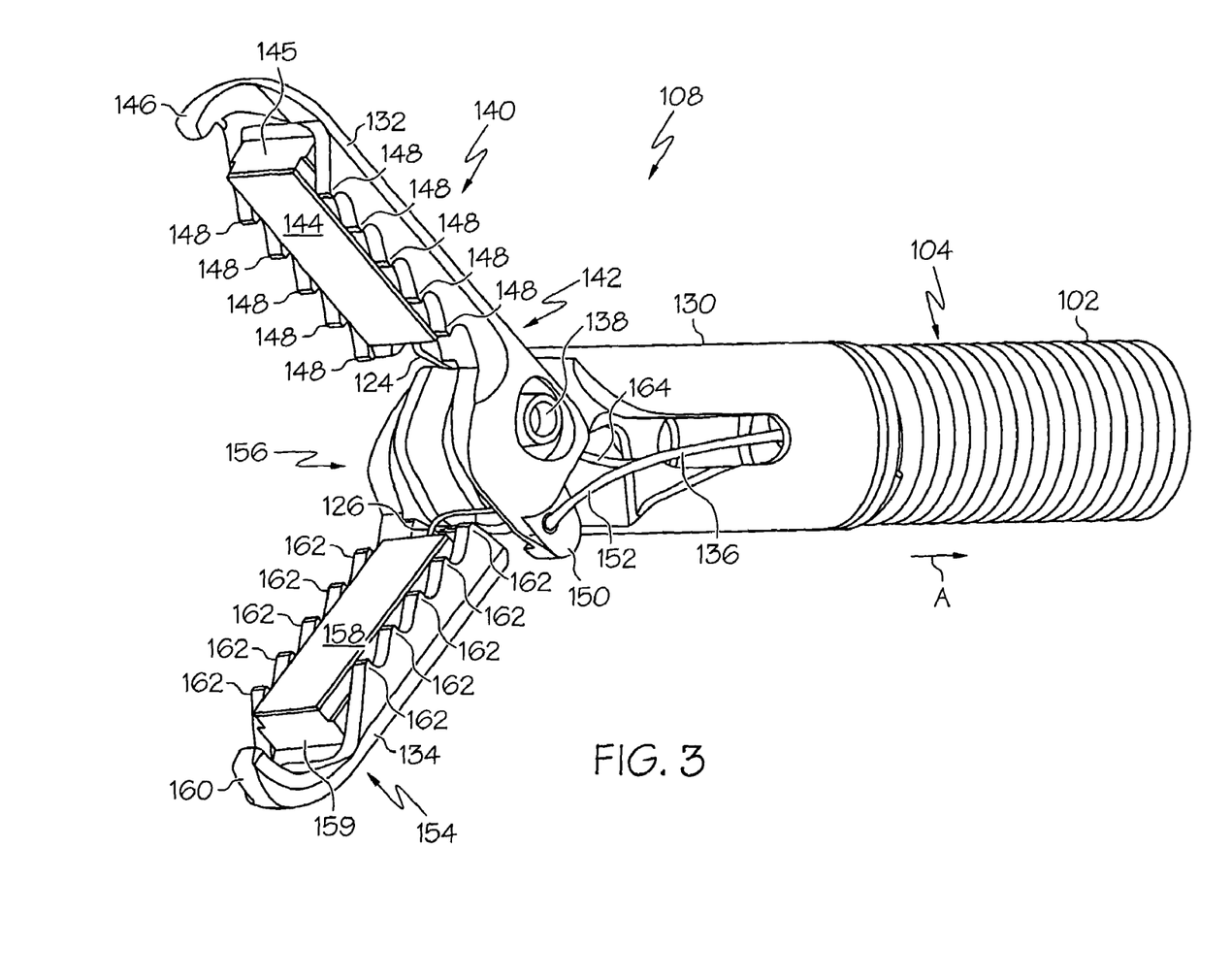
FIG. 3 is a perspective view of one aspect of the working end of the bipolar forceps of FIG. 1 in an open configuration.
Figure 4:
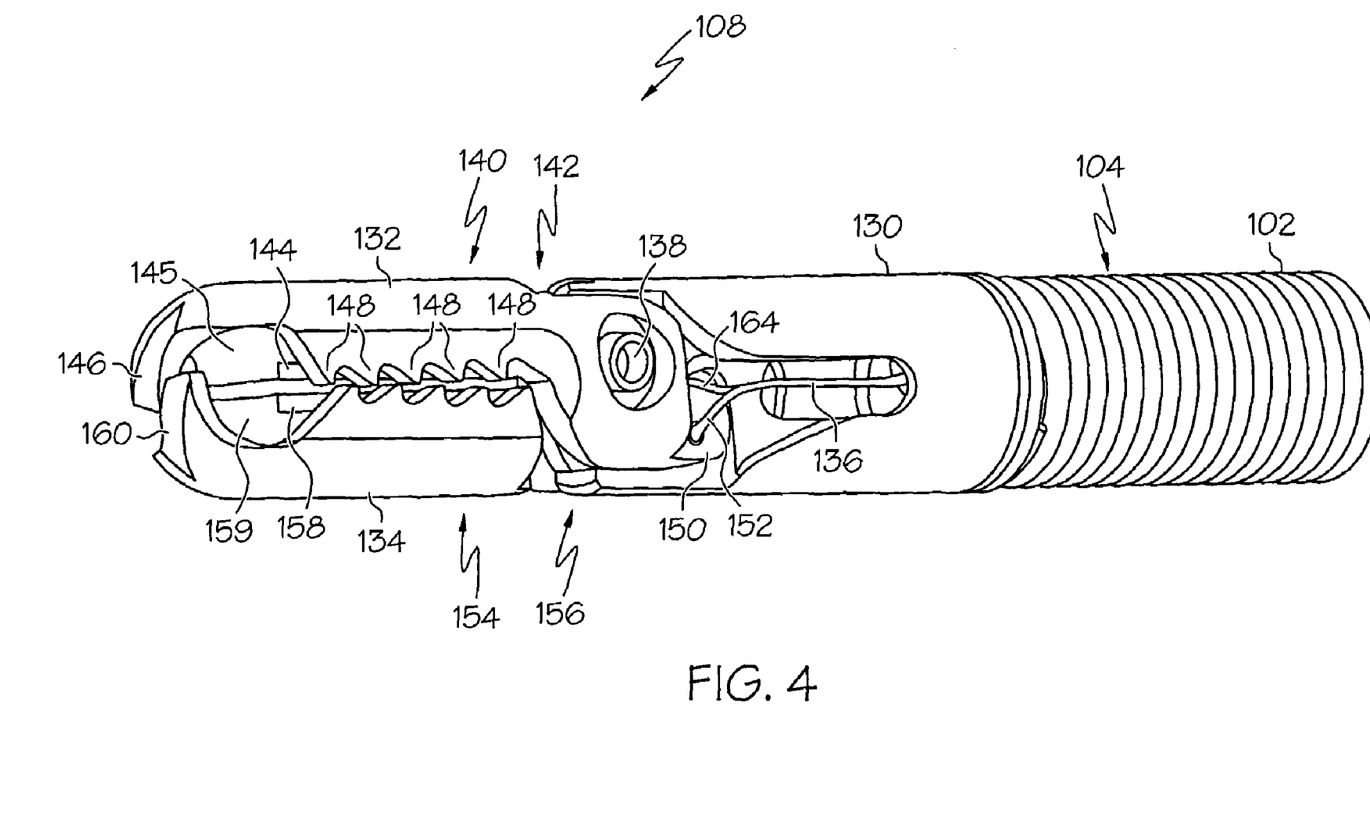
FIG. 4 is a perspective view of the bipolar forceps of FIG. 3 in a closed configuration.

Referring to FIGS. 3 and 4, one aspect of the disclosed grasping/coagulation assembly, generally designated 108, may include a base member 130, a first jaw member 132, a second jaw member 134 and an actuation cable 136. The base member 130 may be connected to the distal end 104 of the shaft 102 and each jaw member 132, 134 may be pivotally connected to the base member 130 at a pivot point 138. The actuation cable 136 may connect the first and second jaw members 132, 134 to the actuator 118 of the handle assembly 110. In one aspect, the electrode wires 124, 126 may function as the actuation cable 136.

The first jaw member 132 may include a grasping portion 140 and a connection portion 142. The grasping portion 140 may include a first electrode 144 and, optionally, an electrically isolating material 145, a nose portion 146 and a plurality of gripping teeth 148. The electrode 144 may be electrically connected to the generator 128 (FIG. 8) by way of the first electrode wire 124. The electrically isolating material 145 may electrically isolate the first electrode 144 from the first jaw member 132. The connection portion 142 may be connected to the pivot point 138 and may include a projection 150 extending proximally from the connection portion 142 for connecting the first jaw member 132 to a first portion 152 of the actuation cable 136.

The second jaw member 134 may include a grasping portion 154 and a connection portion 156. The grasping portion 154 may include a second electrode 158 and, optionally, an electrically isolating material 159, a nose portion 160 and a plurality of gripping teeth 162. The electrode 158 may be electrically connected to the generator 128 (FIG. 8) by way of the second electrode wire 126. The electrically isolating material 159 may electrically isolate the second electrode 148 from the second jaw member 134. The connection portion 156 may be connected to the pivot point 138 and may include a projection (not shown) extending proximally from the connection portion 156 for connecting the second jaw member 134 to a second portion 164 of the actuation cable 136.

The first and second jaw members 132, 134 may be biased to the open configuration shown in FIG. 3 by, for example, a coil spring (not shown) or other biasing device. The first and second jaw members 132, 134 may be approximated to the closed position (FIG. 4) in a grasping-type action by urging the actuation cable 136 in the direction shown by arrow A (e.g., by actuating the actuator 118) such that the jaw members 132, 134 rotate about the pivot point 138. In the closed configuration, the nose portion 146 of the first jaw member 132 may overlap with the nose portion 160 of the second jaw member 134 and the first and second electrodes 144, 158 may be generally parallel and aligned with each other.

In one aspect, the jaw members 132, 134 may be formed from electrically conductive material, such as surgical grade stainless steel, copper, gold, silver, platinum or the like, and may be electrically isolated from each other and/or the electrodes 144, 158. In another aspect, the jaw members 132, 134 may be formed from non-conductive material, such non-conductive fiberglass, various polymeric materials or the like.

The electrically isolating material 145, 159 may be formed from any electrically isolating material, such as rubber, non-conductive polymers or the like. Therefore, in one aspect, traditional, non-bipolar forceps may be easily converted into the disclosed bipolar forceps 100 by connecting electrodes 144, 158 to the jaw members 132, 134 such that the electrodes are electrically isolated from the jaw members with electrically isolating material 145, 159.

The electrodes 144, 158 may be formed from an electrically conductive material and may be electrically isolated from each other and, optionally, from the jaw members 132, 134. In one aspect, the electrodes 144, 158 may be formed from surgical grade stainless steel, copper, gold, silver, platinum or the like. In another aspect, the electrodes 144, 158 may be generally flat, rectangular pads of electrically conductive material separated from the jaw members 132, 134 by an electrically insulating material (not shown).

Figure 5:
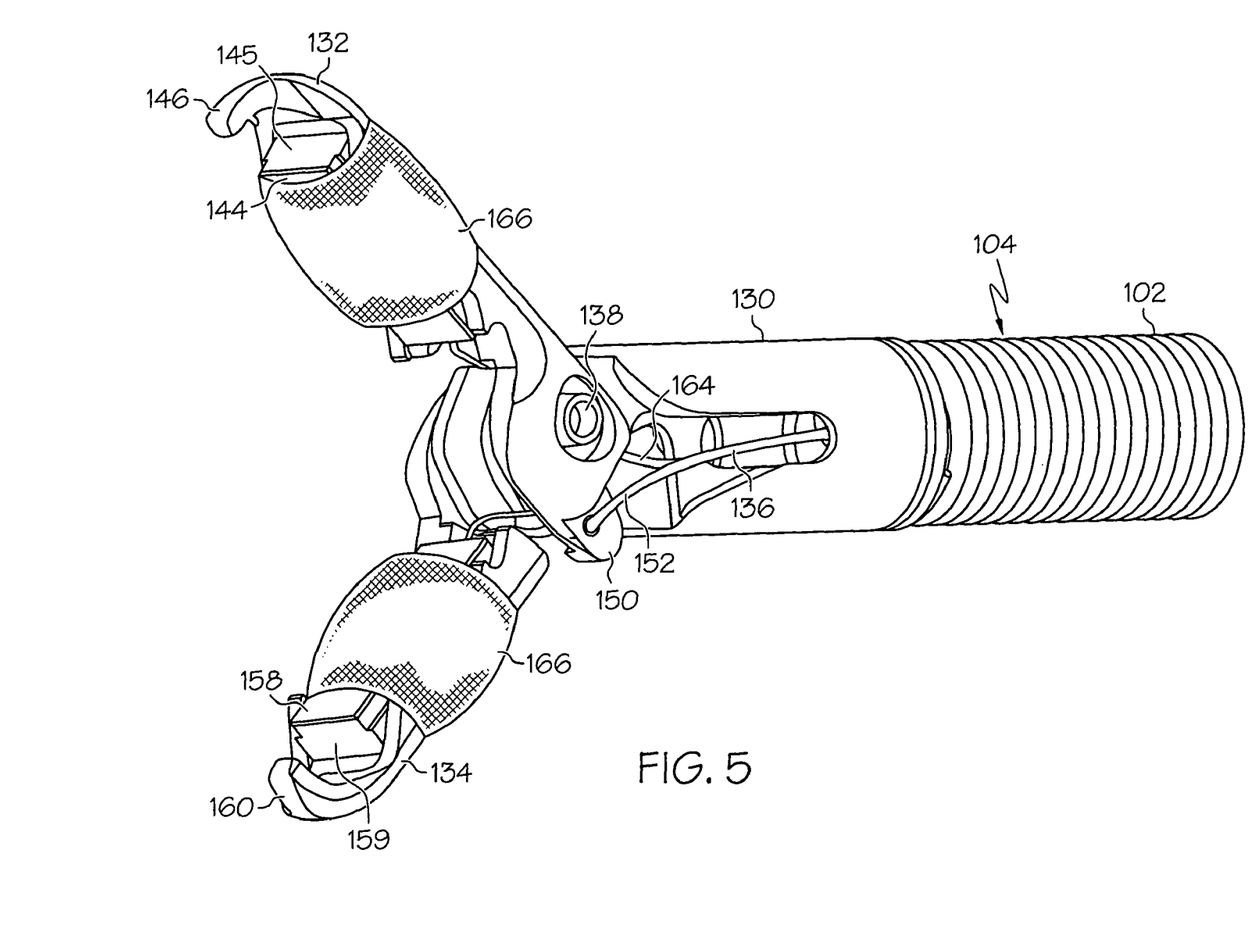
FIG. 5 is a perspective view of the bipolar forceps of FIG. 3 including an absorbent material according to an aspect of the disclosed apparatus and system.

As shown in FIG. 5, each (or only one or more) of the jaw members 132, 134 may include a portion of absorbent material 166 positioned over at least a portion of the associated electrode 144, 158. In one aspect, the absorbent material 166 may be a sponge material (e.g., a natural or synthetic sponge material) disposed over the associated jaw member 132, 134, thereby covering the associated electrode 144, 158. In another aspect, the absorbent material 166 may be a portion of sterile gauze wrapped around the associated jaw member 132, 134.

In one aspect, the absorbent material 166 may be saturated, either partially or completely, with an electrically conductive saturating fluid, such as sterile saline or the like. For example, the working channel 112 of an endoscope 114 (FIG. 8) may be filled with the fluid such that, as the device 100 passes through the working channel 112, the absorbent material 166 absorbs the fluid.

Figure 9:
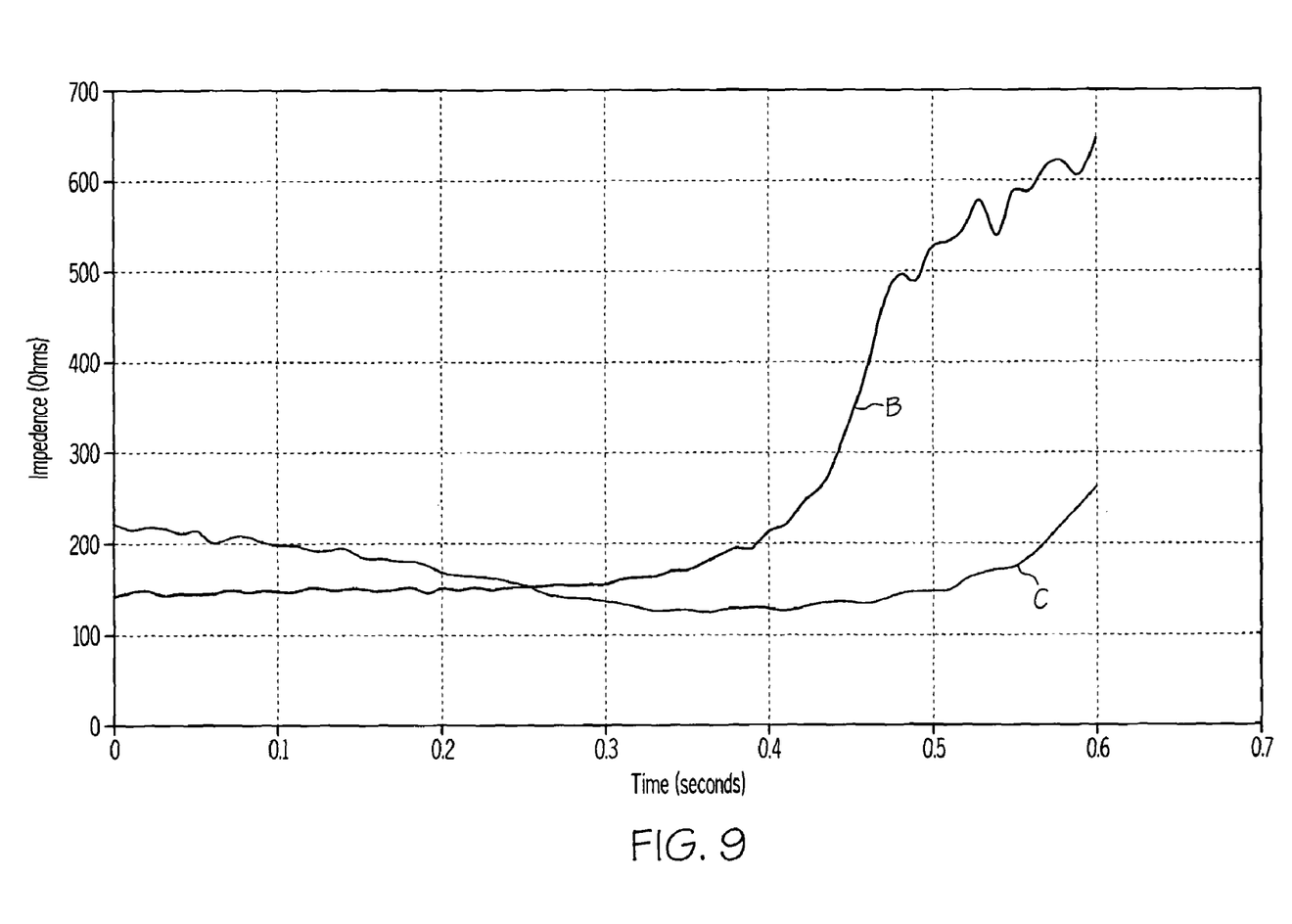
FIG. 9 is a graphical comparison of tissue impedance using the device of FIG. 3 and the device of FIG. 5.

Thus, when the absorbent material 166 is saturated, as described above, the temperature between the electrodes 144, 158 during coagulation may be maintained relatively constant and/or below a predetermined maximum temperature. For example, when the absorbent material 166 is saturated with sterile saline, the coagulation temperature may remain generally at or below about 100° C. (i.e., the boiling point of water). Furthermore, positioning saturated absorbent material 166 between the electrodes 144, 158 and the target tissue 115 may reduce the risk of the target tissue sticking to the electrodes during coagulation. Still furthermore, as shown by lines B (i.e., with saturated absorbent material) and C (i.e., without saturated absorbent material) in FIG. 9, the impedance range of the target tissue 115 may be reduced and may rise more rapidly when using the disclosed bipolar forceps 100 with a soaked absorbent material 166 positioned over the electrodes 144, 158, thereby reducing the risk of applying an excess amount of power to the target tissue.

Figure 6:
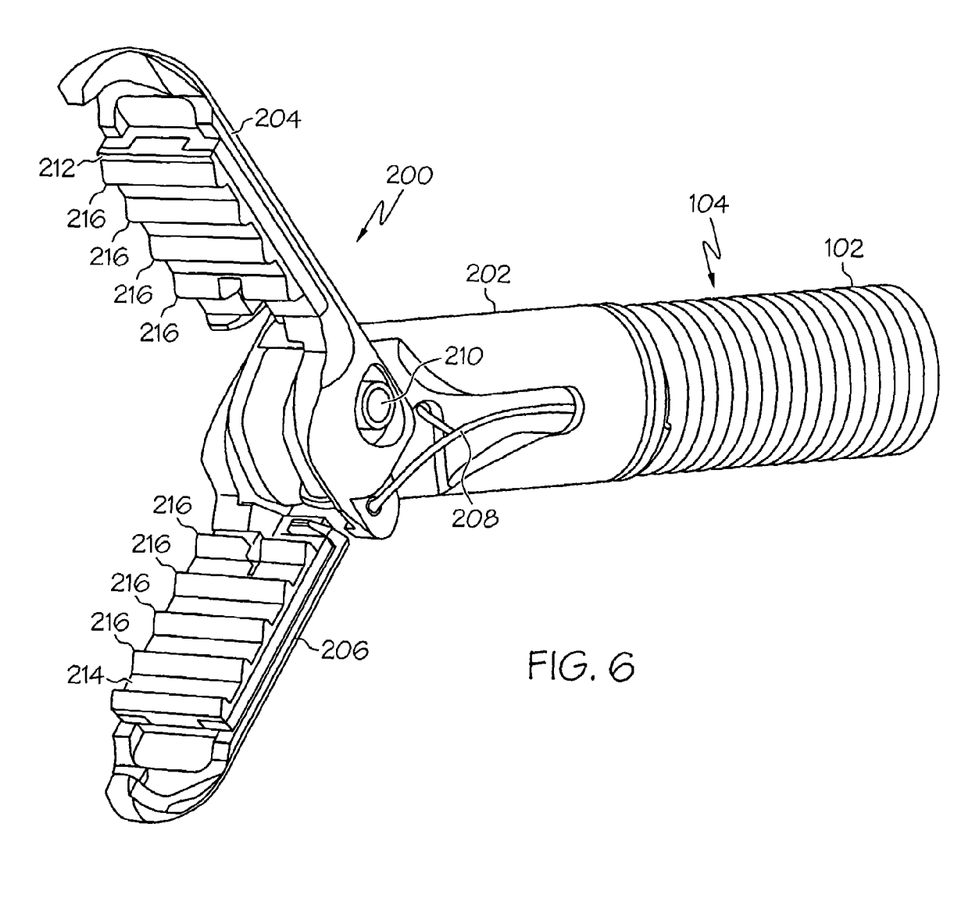
FIG. 6 is a perspective view of a second aspect of the working end of the bipolar forceps of FIG. 1 in an open configuration.
Figure 7:
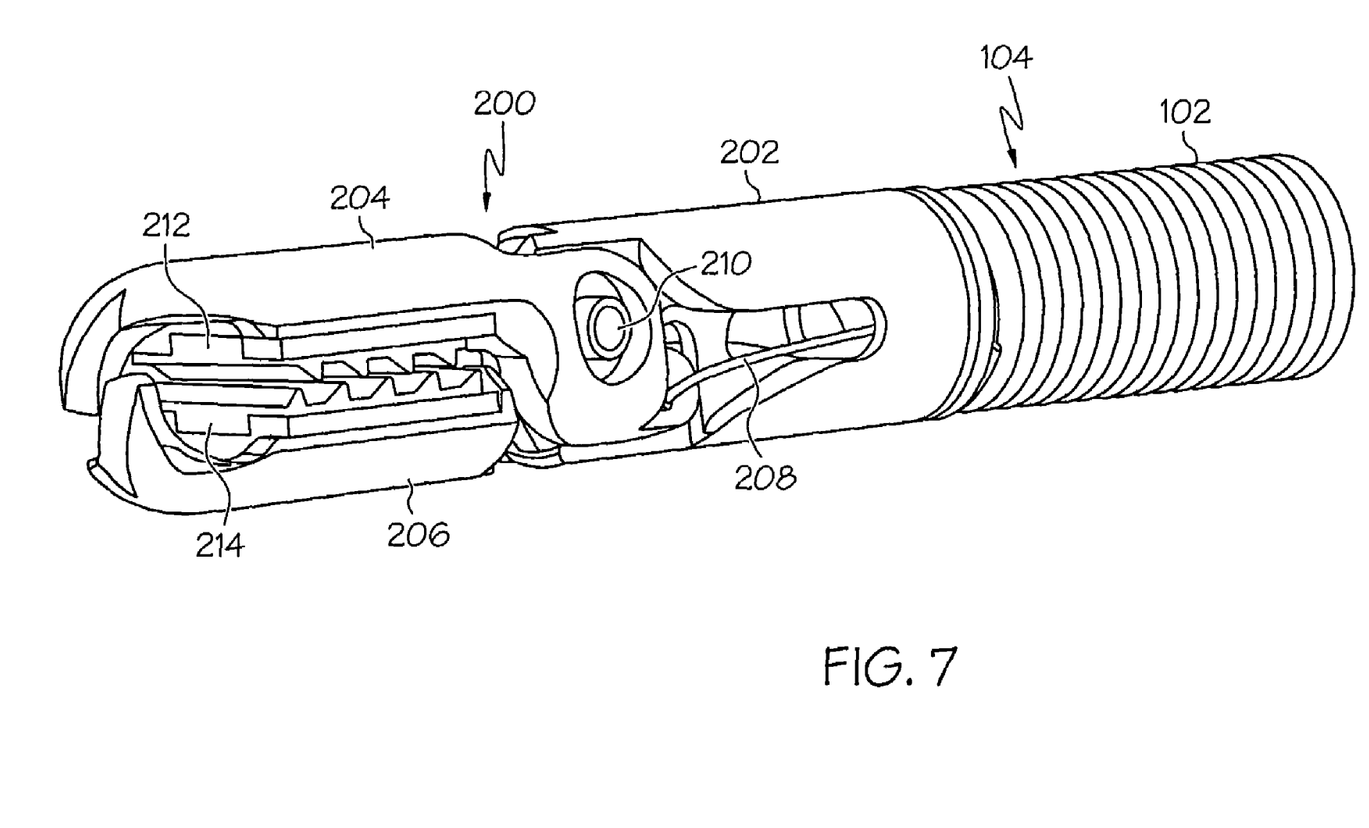
FIG. 7 is a perspective view of the bipolar forceps of FIG. 6 in a closed configuration.

Referring to FIGS. 6 and 7, an alternative aspect of the disclosed grasping/coagulation assembly, generally designated 200, may include a base member 202, a first jaw member 204, a second jaw member 206 and an actuation cable 208. The base member 202 may be connected to the distal end 104 of the shaft 102 and each jaw member 204, 206 may be pivotally connected to the base member 202 at a pivot point 210. The actuation cable 208 may connect the first and second jaw members 204, 206 to the actuator 118 of the handle assembly 110.

Each jaw member 204, 206 may include an electrode 212, 214 connected thereto. The electrodes 212, 214 may be electrically connected to the generator 128 (FIG. 8) by way of the first and second electrode wires 124, 126 and may be electrically isolated from each other and, optionally, the jaw members 204, 206.

The electrodes 212, 214 may be formed from an electrically conductive material, such as surgical grade stainless steel, copper, gold, silver, platinum or the like, and may include a plurality of grasping ridges 216. The grasping ridges 216 may have any size and shape adapted to facilitate grasping target tissue 115 positioned between the jaw members 204, 206.

Accordingly, the bipolar devices and associated systems disclosed herein may provide a user (e.g., a physician) with surgical tools for applying mechanical tamponade (e.g., by way of the grasping-type action described herein) and bipolar electrical energy (e.g., by way of the electrodes) to target tissue. In one aspect, a user may apply bipolar electrical energy while simultaneously applying a mechanical clamping force, thereby providing improved homeostasis results.

Although various aspects of the disclosed bipolar forceps and associated systems and methods have been shown and described, modifications may occur to those skilled in the art upon reading the specification. The present application includes such modifications and is limited only by the scope of the claims.

What is claimed is:

1. A surgical system comprising:
    a source of electrical energy, said source including a first electrical connection and a second electrical connection;
    a first jaw member including a first gripping portion and a first connection portion, said first gripping portion including a first electrode electrically connected to said first electrical connection, a first curved nose portion extending from a distal end of said first gripping portion, and at least two rows of gripping teeth, wherein said first electrode includes a first pad of electrically conductive material and is disposed between said rows of gripping teeth;
    a second jaw member including a second gripping portion and a second connection portion, said second gripping portion including a second electrode electrically connected to said second electrical connection, a second curved nose portion extending from a distal end of said second gripping portion, and at least two rows of gripping teeth, wherein said second electrode includes a second pad of electrically conductive material and is disposed between said rows of gripping teeth of said second gripping portion; and
    an elongated shaft having a distal end and a proximal end, wherein said first and second connection portions are pivotally connected to said distal end of said shaft such that said first and second gripping portions are moveable between an open configuration and a closed configuration, wherein, in said closed configuration, said first curved nose portion is overlapped with said second curved nose portion and said first electrode is aligned with said second electrode.

2. The system of claim 1 wherein said source of electrical energy is a source of bipolar electrical energy.

3. The system of claim 1 wherein said shaft is flexible.

4. The system of claim 1 wherein said shaft and said first and second jaw members are sized to pass through a working channel of an endoscope.

5. The system of claim 1 wherein said first electrode includes at least one of a surgical grade stainless steel, copper, gold, silver and platinum.

6. The system of claim 1 wherein said first jaw member is biased away from said second jaw member.

7. The system of claim 1 further comprising an absorbent material disposed over at least a portion of at least one of said first and second electrodes.

8. The system of claim 7 wherein said absorbent material includes at least one of a sponge material and a gauze material.

9. The system of claim 7 wherein said absorbent material is at least partially saturated with a fluid.

10. The system of claim 7 wherein said absorbent material is wrapped around each of said first and second jaw members.

11. The system of claim 1 further comprising a handle assembly disposed at said proximal end of said shaft, said handle assembly including an actuator operatively connected to at least one of said first and second jaw members.

12. The system of claim 11 further comprising an actuation cable connecting said actuator to at least one of said first and second jaw members.

13. The system of claim 12 wherein said actuation cable electrically connects said at least one of said first and second jaw members to said source of electrical energy.

* * * * *